United States Patent
Kapoustin et al.

(10) Patent No.: US 10,855,957 B2
(45) Date of Patent: Dec. 1, 2020

(54) WIRELESS AUGMENTED VIDEO SYSTEM AND METHOD TO DETECT AND PREVENT INSURANCE BILLING FRAUD AND PHYSICAL ASSAULT FOR REMOTE MOBILE APPLICATION

(71) Applicants: Michael Kapoustin, Osprey, FL (US); Shem Lachhman, Osprey, FL (US)

(72) Inventors: Michael Kapoustin, Osprey, FL (US); Shem Lachhman, Osprey, FL (US)

( * ) Notice: Subject to any disclaimer, the term of this patent is extended or adjusted under 35 U.S.C. 154(b) by 0 days.

(21) Appl. No.: 16/170,078

(22) Filed: Oct. 25, 2018

(65) Prior Publication Data
US 2020/0137357 A1    Apr. 30, 2020

(51) Int. Cl.
| | |
|---|---|
| H04N 7/18 | (2006.01) |
| G16H 40/20 | (2018.01) |
| H04W 12/00 | (2009.01) |
| G06Q 30/00 | (2012.01) |
| H04N 5/232 | (2006.01) |
| G06K 9/00 | (2006.01) |
| G08B 21/02 | (2006.01) |

(Continued)

(52) U.S. Cl.
CPC ......... *H04N 7/185* (2013.01); *G06K 9/00013* (2013.01); *G06K 9/00255* (2013.01); *G06K 9/00604* (2013.01); *G06Q 30/0185* (2013.01); *G08B 21/02* (2013.01); *G16H 40/20* (2018.01); *H04N 5/23238* (2013.01); *H04W 4/021* (2013.01); *H04W 12/00508* (2019.01); *G06Q 40/08* (2013.01)

(58) Field of Classification Search
CPC ... H04N 7/185; H04N 5/23238; H04W 4/021; H04W 12/00508; G06K 9/00013; G06K 9/00255; G06K 9/00604; G08B 21/02; G16H 40/20; G06Q 40/08; G06Q 30/0185

See application file for complete search history.

(56) References Cited

U.S. PATENT DOCUMENTS

| | | | |
|---|---|---|---|
| 9,836,054 B1 * | 12/2017 | Lema | ................... G05D 1/0088 |
| 9,912,901 B2 | 3/2018 | Thompson | |
| 2015/0324528 A1 | 11/2015 | Chang | |

(Continued)

FOREIGN PATENT DOCUMENTS

EP    3122201 A2    2/2017

*Primary Examiner* — Nasim N Nirjhar

(57) ABSTRACT

The present invention discloses a wireless augmented video system and method to monitor medical insurance billing fraud, drug or other theft and elder patient or child abuse by the caregivers. The wireless augmented system comprises; a wireless augmented monitoring devices, a cloud system monitoring center and a caregiver employing agency. The wireless wearable augmented monitoring devices further includes a smart wearable nametag apparatus and smart wearable wristband. A wireless cellular transceiver configured within the nametag apparatus to stream the augmented video stream in response to an event detected. The nametag apparatus also incorporates a memory element to buffer the augmented data prior to transmission, a SIM card to connect to any data cellular network, a Bluetooth to connect peripheral devices, a Wi-Fi component, color LCD screen for displaying current caregiver's name and photograph on the name tag, and LED power status display, a microphone, speaker and a micro USB port.

5 Claims, 8 Drawing Sheets

(51) Int. Cl.
*H04W 4/021* (2018.01)
*G06Q 40/08* (2012.01)

(56) References Cited

U.S. PATENT DOCUMENTS

| | | | |
|---|---|---|---|
| 2015/0348001 A1* | 12/2015 | Van Os | G06Q 20/322 |
| | | | 705/44 |
| 2016/0072802 A1* | 3/2016 | Hoyos | H04L 63/0861 |
| | | | 726/5 |
| 2016/0239612 A1 | 8/2016 | Barry | |
| 2018/0090229 A1* | 3/2018 | Sanyal | G16H 80/00 |
| 2019/0231707 A1* | 8/2019 | Stiles | A61B 5/117 |
| 2019/0342223 A1* | 11/2019 | Dhanabalan | H04L 47/28 |

* cited by examiner

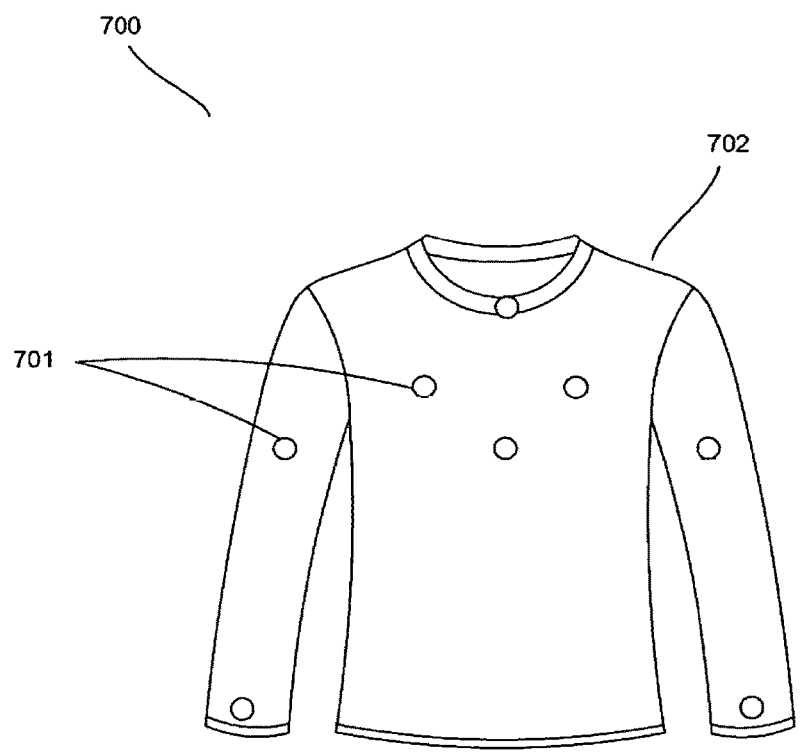
FIG. 7
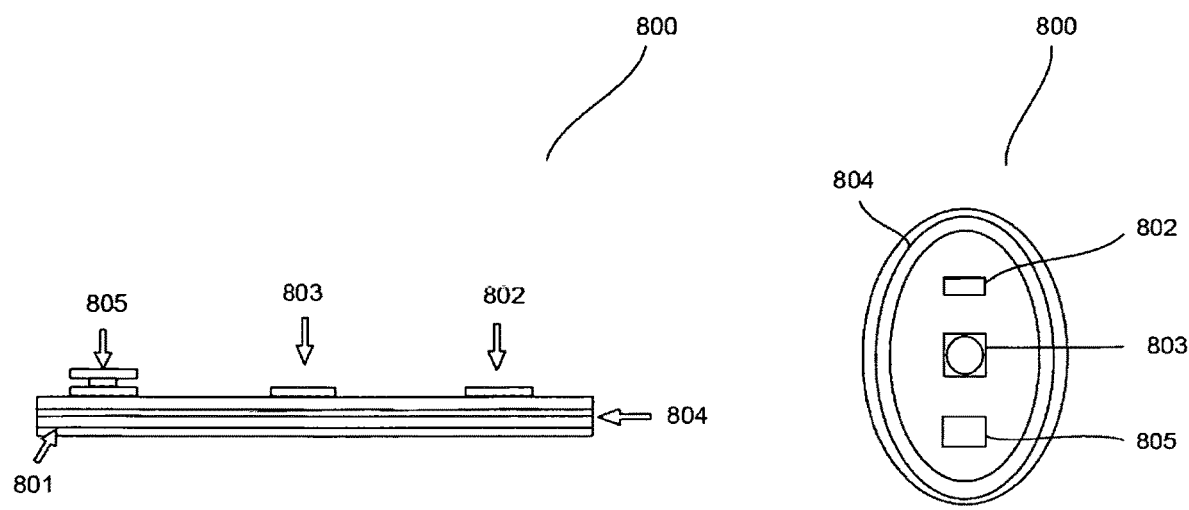
FIG. 8A
FIG 8B

WIRELESS AUGMENTED VIDEO SYSTEM AND METHOD TO DETECT AND PREVENT INSURANCE BILLING FRAUD AND PHYSICAL ASSAULT FOR REMOTE MOBILE APPLICATION

FIELD OF THE INVENTION

The present invention relates to a remote caregiver monitoring system and method, and more particularly, an augmented real time multiple video streams that provide geospatial motion detection and thermodynamics monitoring and biometric data as encrypted actionable intelligence on the identity, actions and movements of one or more caregivers in confined spaces to detect possible medical insurance billing or physical abuse as they interact with patients.

BACKGROUND OF THE INVENTION

Today, there is a major shift towards "aging in place" as most adults prefer the comfort and privacy of their own homes for as long as possible. The result is that healthcare in the home is now an increasing focus for members of the public, whether as patients, family members, relatives or friends; healthcare professionals; politicians; healthcare administrators; and the media. The public focus is not on cost savings, but rather on the personalization of institutions and the public expectation that care would be better at home.

Development in technologies are also driving the change in sites of care from the acute care hospital to many other settings including long term care settings, nursing homes, group homes, daycare and care in the home. Public spending on federal healthcare programs is growing rapidly, primarily driven by (1) the rising enrollment-streaming from the aging of the population and (2) expansion of federal abuse and its prevention programs increasing the spending per enrollee.

According to one survey National health expenditure for elderly care in the U.S alone was worth more than $300 billion in 2016. It is estimated by the U.S Census Bureau that in the year 2050, there will be 83.7 million people in the United States alone who will be 65 years old or older.

This rapid growth in federal and state funding of home care has seen an increase in the number of agencies and caregivers required to service a growing public demand for in-home health care. A consequence of this growth is a greater frequency of compliance and billing concerns leading to fraud and elder abuse. Home health has long been recognized as a program area vulnerable to fraud, waste and abuse.

State and federal funding to aged care providers is delivered in three streams: behavioral assistance, physical assistance, and complex care needs.

All these three streams are delivered to elders and the disabled in private homes or assisted living facilities. In all three cases caregivers spend significant amounts of unmonitored time alone with the person under their care.

There is caregiver interaction when alone with a patient. The absence of any reliable caregiver and patient real time monitoring tool, provides opportunity for both fraud and elder abuse. The government centers for Medicare (CMS), state Medicaid agencies (SMA) and the Medicaid Fraud Control Units (MFCU) of the US government have committed significant financial and human resources to advancing the fight against the home health fraud, waste, physical and mental abuse. They have mandated to partner with private sector partners to save and recoup taxpayer money.

The aggregate financial loss to government and the private sector is estimated in the tens of billions of dollars annually. In fiscal 2015, the CMS estimated that government agencies alone made more than $10 billion improper payments to home healthcare agencies resulting in more than 350 criminal and civil actions that year alone.

Collaboration with private sector partners is critical for development of hardware and software tools capable of (1) detecting billing fraud at the source and in real time when committed by caregivers or homecare agency providers when reporting billing hours or services delivered by otherwise unmonitored caregivers; (2) deterring physical and mental abuse of patients by unmonitored caregivers; (3) preventing occurrence of false claims by patients or family members of alleged physical and mental abuse by an unmonitored caregivers.

The principle problem with current billing fraud detection methods is that detection occurs only after the fact of an insurance payment and looks for a long pattern of accounting anomalies making it unreliable, slow and costly. Current fraud detection, reporting and investigative methodologies, strategies and techniques exclusively rely on accounting entries and a pattern of statistically significant fraudulent payouts to occur before detection is possible. Again the problem with this current method of data analysis, statistical sampling, predictive modeling and investigation support analytics to uncover health care billing fraud detection is that it is possible only after the fact of a payout. As a result, this requires taxpayers and private insurers to suffer significant financial losses before statically significant accounting data is collected for any successful incorporation into a criminal or civil case thereby making the recovery of taxpayer money unlikely and prevention almost impossible.

Furthermore, current government methods of data analytical techniques cannot visualize physical or mental abuse of patients by caregivers as a pattern, and cannot prove or disprove claims of physical or mental abuse.

Additional problems include caregiver dependent time and location tracking authentication system collecting billing and services data that cannot be independently or objectively confirmed. Real time data being reported to and under the exclusive control of a person or company committing the fraud or abuse. These private sector devices and software application solutions collect caregiver GAS tracking, time management and reporting information using personal devices provided to the caregiver. The key problems with current industry solutions are: poor user authentication as devices are not securely paired to an individual caregiver; the need for proactive action on the part of caregiver to (a) activate the device and (b) enter time and service data into the device; remotely collected data which is received only by the caregiver's employer and therefore not subject to an independent verification, the majority of medical insurance billing fraud is on the part of the employing home healthcare agency; any personal mobile device software applications and standard operating system [OS] is easily spoofed; and none of the current solutions monitor the conduct of the caregiver with the patient.

Another key problem is that the collected or reported data by these personal devices is not securely paired to the caregiver during registration, authentication or use. The current devices used to collect billing or services data from a particular caregiver lack secure multi-factor data, devices and caregiver identification pairing where the data and device are paired to particular caregiver and patient authentication and/or lack independent and real time service validation before payment is rendered to the caregiver or the private home healthcare agency by the government insurer or private payer. This security failure leaves the door open to fraudulent criminal activity.

The most significant single problem with current methods and technologies is that there is no device, no software and no established methods for the real time detection and recording of mental or physical abuse during caregiver and patient interactions. There is no wearable home healthcare device for monitoring and reporting abuse of patients and the elderly.

Therefore, there is a need of a system that solve the above-mentioned problems by outfitting caregivers and patient homes and rooms with a smart device that can track, monitor and analyze caregiver and patient geospatial movement and interactions within the immediate area of the caregiver and patient using a number of sensors, and to then encrypt, compress, buffer and then securely transmit the collected data as a real time augmented video data stream carrying real time actionable intelligence. Further there is a need of such a system to provide secure cloud storage and continuous monitoring from a remote location tagging the collected data with the unique biometric information of the caregiver and their exact geo-location.

SUMMARY OF THE INVENTION

The present invention relates to a caregiver remote geospatial tracking and monitoring system or a system for monitoring home healthcare agency personnel, the operators or caregivers at a plurality of private patient homes and at other locations of patients using associated devices paired to the system that monitor, track, record and analyze real time geospatial data on movement, buffers and then securely transmits the data as actionable real time intelligence as video, audio and other sensory data collected by the device within the immediate environment of the caregiver and their direct field of vision. According to an embodiment, the devices are a mobile monitoring and reporting apparatuses equipped with a multitude of biometric sensors, and electronic modules to detect, record and report instances of insurance billing fraud, property or prescription drug theft, health risk to patient or recipient of their services and cases of elder or child abuse.

The system of said invention is equipped with devices worn by or within the immediate proximity of the caregiver and able to collect a multitude of geospatial, thermal, biometric and biomechanical data necessary to establishing and recording a pattern of geospatial movements made as a caregiver provides a medical treatment or non-medical service; and to determine from the collected data if the observed real time pattern of movement falls within acceptable tolerances for similar stored geospatial and thermal data know to be empirically consistent with such movements during the delivery a particular medical treatment or non-medical service. For an example, in one instance, a physician may order physical therapy. the devices of the system use cameras to tracks geospatial movement and human thermodynamic flow, with biometric and biomechanical data to compare with the systems database and confirm that a caregiver is in fact performing the physical therapy. Simultaneously, the system is capable to track other data such as GPS location, or departure and arrival times along with audio and visual data which can be correlated with the biomechanical movements of the caregiver to ensure that the caregiver is performing his or her duties as ordered required according to an approved plan of care. Additionally, the system sends alter notifications to monitoring station if its analysis of the data via machine learning artificial intelligence and analytical models detects any mismatch between the collected real time tracking data on caregiver and patient movement, biometrics and spatial interactions with the medical insurance billing code paired to such data.

In addition to tracking caregiver geospatial movements and interactions with the patient to ensure there is no activity that suggests possible medical insurance billing fraud, the system uses the same cameras and audio data to track geospatial movement and human thermodynamic flow, biomechanical, and empirical data for detection of the possible physical or mental abuse of the patients. In many instances, caregivers are found to repeatedly deliver physical abuse to patients. To insure the safety and well being of the patient, the described invention will detect possible elder abuse using real time data collected via the monitoring devices tracking and recording the geospatial and biomechanical movements of the caregiver in proximity to the patient within the GPS fenced and digitally mapped location; biometric information is used to identify the specific caregiver and patient. Each group of information or data taken of the caregiving environment or the caregiver or patient is analyzed and compared repeatedly for possible signs of possible abuse of a patient.

The invention discloses a wireless augmented video system used to digitally capture and record a visual and thermal map of all objects in its immediate surroundings, including caregivers and patients and to track the geospatial movements and interactions of these objects in that space compared to previously learned information in the system database searching for anomalies that might suggest possible medical insurance billing fraud, property or prescription drug theft, a health risk to a patient or an instance elder or child abuse. The wireless augmented video system comprising of; different embodiments of wireless augmented monitoring devices worn by the caregiver to monitor caregiver actions, patient well-being, and the caregiving environment to detect possible patient abuse and healthcare billing fraud which are: smart nametag apparatus, smart wearable wristband, a neck wearable device, Ear worn device or a combination thereof; and cloud system monitoring center to monitor, store and analyze the real time augmented data from the monitoring device to detect fraud or abuse and inform such to the employer of the caregiving personnel, government organization and other personnel paying the bills.

Each device of the invention are different embodiments of a wireless augmented device that contains a plethora of sensors to both track statistics of the caregiver, the caregiving environment, and the client or recipient of services. An imperative feature of the devices is its ability to be non-reliant on local Wi-Fi networks, or user operation. The devices of the invention will always contain supporting electronics to connect to a 4G/LTE network or better. This is to ensure that the user, in this case a caregiver, cannot interfere, damage, turn-off, or interrupt monitoring of the environment or themselves.

The smart nametag apparatus of wireless augmented monitoring devices is a compact body wearable box like apparatus comprising within an embodiment of; a processor, a Bluetooth module, a rechargeable battery, an internet module, a Wi-Fi module, a RFID receiver, a wide angle cameras, microphone and speakers, Face to face IR camera with light, a LTE network connection module, set of indication LED lights, a fingerprint scanner, a color touch display, a thermal imaging camera with IFR lights, GPS module, USB and power ports and micro HDMI port. While the wireless wearable wristband of the augmented monitoring devices comprises of plurality of different sensors to collect and transmit geospatial movements and biometric information of the caregiver in real time for analysis toward the detection the elder or abuse as well billing fraud and drug theft which are; photoplethysmography sensor which measures blood volume pulse (BVP) from which heart rate, heart rate variability (HRV) and other cardiovascular features are collected; a 3-axis accelerometer captures motion-based activity, to report disturbance in the caregiver's balance such as fall; (3) an EDA sensor (GSR sensor) electrodermal activity sensor used to measure sympathetic nervous system arousal and to derive features related to stress, engagement and excitement; an infrared thermopile that reads peripheral skin temperature, to detect, among other things, fever; and a transdermal transmission sensor to measure blood alcohol levels. The neck wearable embodiment of the augmented device also comprises multitude of sensors ranging from electrode arrays, optical, visual, location, vibration and position sensors while the ear wearable embodiment of the device equipped with a visual sensor, to take thermo-graphic imaging and near infrared imaging of the client or recipient of services, optical sensor and inner ear optical sensor.

The wireless augmented monitoring devices are small light weight mobile monitoring and reporting apparatuses relying on the LIE: data network for use in homes, nursing or healthcare facilities and child daycare centers. The monitoring devices manages all the monitoring, analyze, recording, reporting and incident alerts in real time and without relying on the integrity or habits of human operators. The monitoring devices continuously monitors the exact time of caregiver coming and goings, as well as all physical actions, motion and movement, and health and mental state of each caregiver(s) entering the pre-defined geo-fenced perimeter assigned to each individual set of monitoring devices. Monitoring, recording, transmitting and analysis functions are activated only after the system detects, verifies and successfully pairs with the wireless wearable devices biometrically associated to a specific caregiver. Once activated by three step biometric authentication, the wireless monitoring devices collects data from multiple biometric, audio visual and geospatial components and sensors embodied within the devices and located within its geo-fenced perimeter, including the infrared captured by its 360 degree camera view and sounds recorded by its directional microphones. All the collected data is analyzed by monitoring devices and monitoring centers against the baseline data of the particular caregiver associated with the wireless sensing and monitoring devices. Certain conditions detected by the monitoring devices triggers audible and silent alerts to responsible persons for intervention. Some of these alert conditions includes but not limited to potential health hazards to a patient or child.

The invention solves medical insurance billing fraud by, inter alia, relying on only real time recorded empirical data collected on site; the data is used to verify or challenge any medical insurance billing request for payment by a medical or non-medical service provider; the collected empirical data is specifically tagged and uniquely encrypted to the one patient, the care or service provider billing code and the specific caregiver present during a treatment or service period are also embedded in the augmented data stream; this uniquely recorded data is also stamped with the exact time, date, location and medical or non-medical treatment service code as submitted by the care provider, the information is managed by an independent monitoring body, a non-government organization; (a) who securely stores and then (b) distributes alerts to all parties when the empirical (i) does not factually correspond to the accounting data as submitted in an medical insurance claim request for payment; (ii) suggests elder or patient physical or mental abuse; and (c) distributes alerts in such cases to authorize persons or bodies, inter alia, (i) the patient, (ii) the physician, (iii) the home healthcare agency, (iv) the family employing the particular caregiver, (v) government and (vi) private sector payers, and (vii) judicial authorities on subpoena.

To guarantee the integrity of the collected data, the invention utilizes among other things, device and data pairing to each current user of the device. The wearable user authentication and pairing process requires (1) multiple biometric keys collected from the caregiver/user at time of registration and later during each activation or login to the device; (2) the post login collection of that particular user caregiver's schedule of (a) patient GPS location; (b) time of service at the location and (c) a series geofencing triggers are all obtained wirelessly from the cloud system and used for self-activation and deactivation of data collection process; the user caregiver has no control over device function; (3) further, self-activation and deactivation of the device can occur according to other changes detected by an array of internal and peripheral sensors.

To additionally guarantee the authenticity of wireless transmitted data, the device embeds as part of an augmented data stream (1) GPS location data; (2) real time biometric information on the caregiver; (3) the unique user biometric identification [UUBID] key collected during login; and (4) the unique user identification [UUID] key of the caregiver's employer.

To additionally guarantee the securing of buffered and the wirelessly transmitted data, the device; (1) compresses and encrypts each data packet or stream before wirelessly transmitting; (2) transmits the encrypted data to an independently operated remote cloud storage and caregiver monitoring facility; (3) the file is then stored utilizing high entropy encryption algorithms, including a quantum key, random number security token, as part of a three key retrieval system where 2 of 3 keys are required to access and decrypt video data.

to additionally guarantee the securing of data buffered by the device, the device only dynamically stores all real time data and then deletes that data, (1) on a verification from the cloud system confirming delivery of the buffered data; (2) in the event of a lengthy timeout in its connection to the cloud system, (3) loss of power and (4) any attempt to tamper with the device instances (2)-(4) initiates an alarm on the device and at the monitoring station.

furthermore, the object of the invention is to provide a wireless augmented video system to collect, record and interpret other forms of environmental data, including but not limited to use of video, image and other biometric data of the caregiver to detect if a patient falls, is physically or mentally abused, unauthorized access, if the caregiver misbehave, fraud and theft etc.

Another objective of the invention is to provide a wireless augmented video system to geo-track and video record each action, location and movement of a specified caregiver including but not limited to use of artificial intelligence and image recognition to determine delivery of care, quality of care, time on site, action on site and possible elder or child abuse.

These and the other aspects of the embodiment herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF DRAWINGS

FIG. 7 illustrates the incorporation of the devices within the clothing to monitor caregiver biometrics and actions.

FIG. 8A illustrates cross sectional view of node and Schematic depicting the form and electronic design of the nodes for a system to detect caregiver actions to prevent elder abuse and healthcare billing fraud.

FIG. 8B illustrates the top view of the node of system.

DETAILED DESCRIPTION OF INVENTION

The embodiment herein and the various features and advantageous details thereof are explained more fully with reference to the non-limiting embodiments and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

According to an embodiment, the present invention provides a system for detection and reporting of insurance billing fraud, physical and mental abuse possibly possibly by the caregivers to the elderly or a child or a patient when providing medical or non-medical care through the use of a cloud data monitoring facility and non-medical wearable monitoring worn as a as a smart nametag apparatus, a wearable wristband, a neck and ear wearable device all of which are just different embodiments of the augmented monitoring device with plethora of sensors and other electronic components to track the geospatial movement and changes in human thermodynamics of the caregiver in the caregiving environment, during interactions with the patient or other recipients of services.

The smart nametag apparatus, in real time, monitors, buffers, and then securely transmits video, audio and ocher sensory data collected by the apparatus within immediate environment of the caregiver and the direct field of view of the apparatus; the collected data is then transmitted and tagged with the caregiver unique biometric information and location, which is then remotely stored and continuously monitored in a secure cloud data monitoring facility.

Figure 1A:
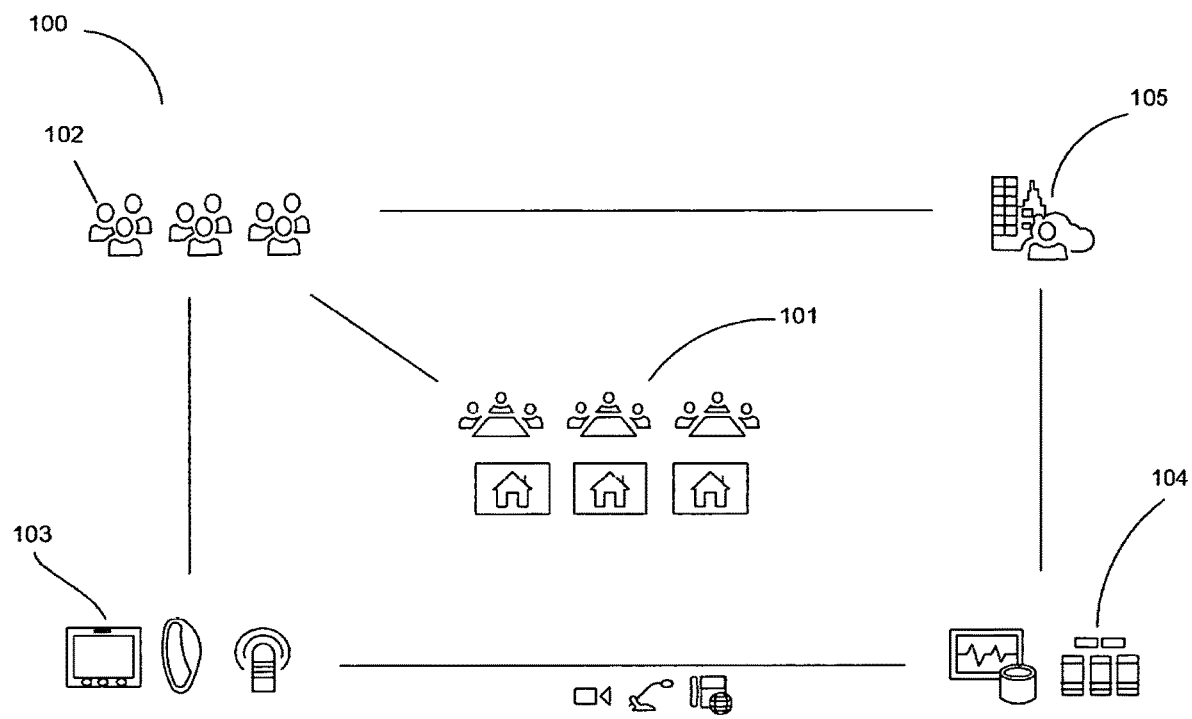
FIG. 1A illustrates a general block diagram of wireless augmented video systems and methods for mobile application of the same for augmented monitoring a caregivers in a plurality of patient locations.

According to FIG. 1A which exemplarily illustrates a caregiver monitoring system 100 to monitor, detect and prevent billing fraud as well as physical and mental abuse of elderly person or patients by the caregivers. The monitoring system 100 of FIG. 1 comprises of a compact wireless augmented monitoring devices 103 having different embodiments such as smart name badge or nametag apparatus, a smart wearable wristband, a neck wearable device and an ear wearable device, a cloud data monitoring facility or monitoring center 104, a patient or elderly person 101 in need of care at home or any remote location, a caregivers 102 and agency or the employers of the caregivers 105. The wireless augmented monitoring devices 103 of system 100 comprises of a plurality of various cameras with lights, microphones, sensors, scanners, GPS, networking and communication units, Bluetooth, storage unit, controller and speaker while the wristband comprises of plurality of biometric sensors that provides data for one stage biometric authentication of the caregiver and real time data of general physical and emotional state of the wearer or caregiver.

According to an embodiment, the caregiver monitoring system 100 requires a wireless augmented monitoring devices 103 of a system 100 to be activated and paired to a caregiver and a licensed home health care operator using a three step biometric authentication and verification process which are fingerprint verification, facial or iris verification and certain unique properties of electrocardiogram and other bodily biometrics. After the biometric authentication of caregiver or licensed home health care operator only, the smart nametag apparatus of the wireless augmented monitoring devices 103 starts monitoring and transmits real time data such as video, audio and other sensory data collected by the devices within the immediate environment of the caregiver and their direct field of vision to the cloud data monitoring center 104 which stores the received data for monitoring and analysis of billing fraud as well as abuse to the patient by the caregiver or the abuse from the patient or family to the caregiver personnel.

Figure 1B:
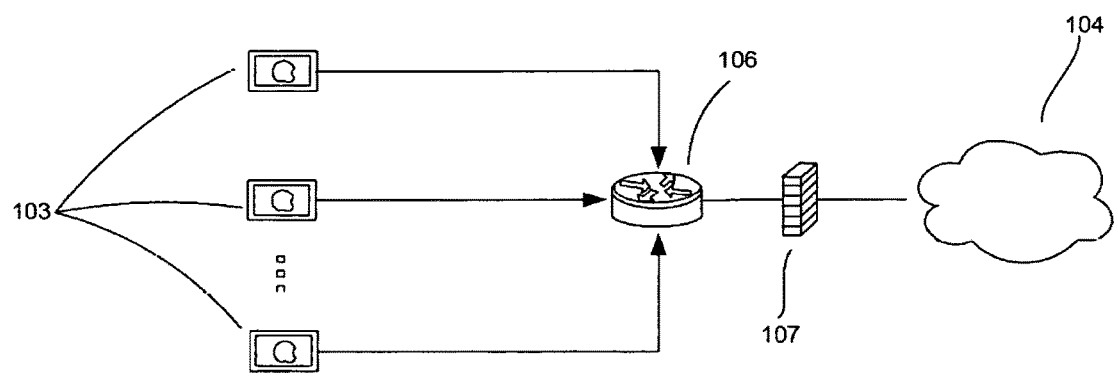
FIG. 1B illustrates diagram of wireless monitoring, collecting and storage of encrypted data of multiple caregivers using smart into the cloud data monitoring facility of a system.

FIG. 1B shows another exemplary embodiment of the present system for wireless monitoring, collecting and storage of encrypted data of multiple caregivers each with a dedicated of augmented monitoring devices 103 into the cloud data monitoring center 104 of a system 100. According to the present exemplary embodiment, multiple dedicated and augmented monitoring devices 103 allotted to multiple individual caregivers are connected to the cloud monitoring and storage 104 through wireless carrier 106 and a firewall 107.

Figure 1C:
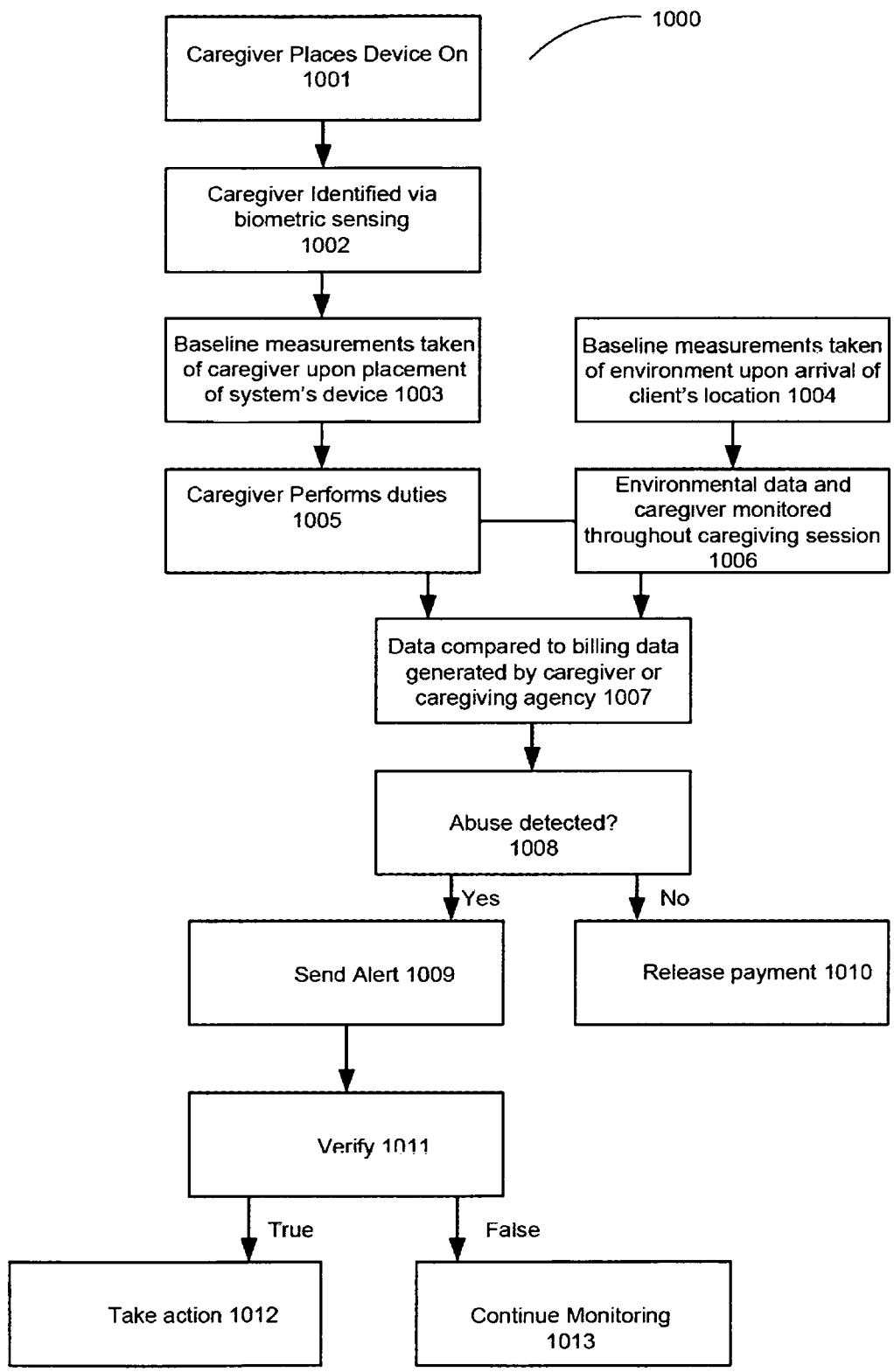
FIG. 1C exemplarily illustrates a block diagram depicting order of operation of the system to detect abuse to the client and billing fraud committed by caregivers or caregiving agencies.

FIG. 1C exemplarily illustrates a block diagram depicting order of operation of the system to detect abuse to the client and billing fraud committed by caregivers or caregiving agencies where caregiver data, caregiving geospatial movement and thermodynamic environmental data, and billing data are compared. Where the sequence of working of system 1000 starts with the placement of the device on the body of the caregiver 1001 according to an embodiment of different devices which then detects for identification and authentication of caregiver via biometric sensing in step of 1002; after the authentication of the caregiver, system starts taking baseline measurements of caregiver upon placements of system's devices 1003 and taking baseline measurements of environment upon arrival of client's location 1004; system detects caregiver geospatial movements, biomechanical and thermodynamic data while performing duties 1005 and environmental data and caregiver monitored throughout caregiving session 1006; which data then compared to billing data generated by caregiver or caregiving agency 1007 to analyze that data in terms to detect abuse 1008; if there is not any abuse then the system allows to release payment 1010 while if it detects an abuse then the system sends alert to the family of the patient, government organization which controls abuse and all other bodies related with system; which is then verified by said monitoring bodies to check whether it is true or false and take action 1012 or continue monitoring 1013 respectively.

Figure 2A:
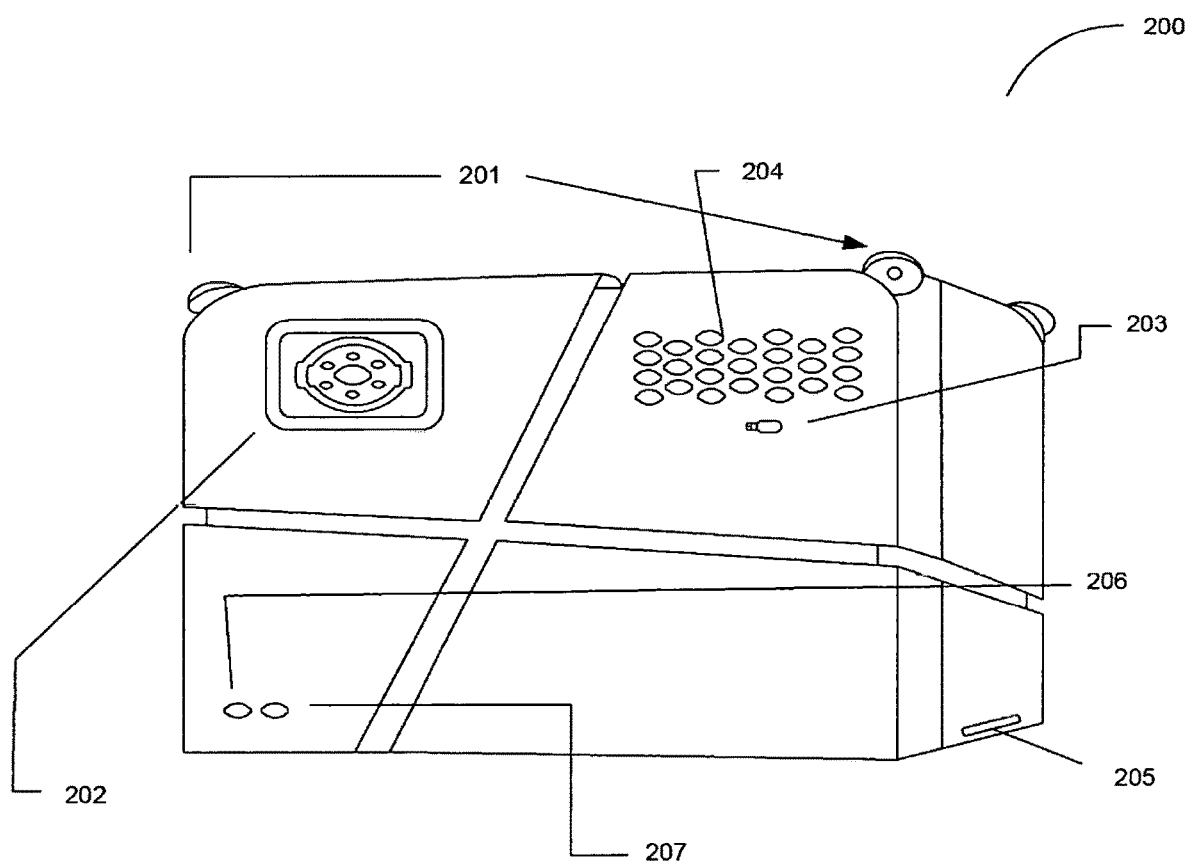
FIG. 2A shows an exemplary smart name tag device box of the augmented system.
Figure 2B:
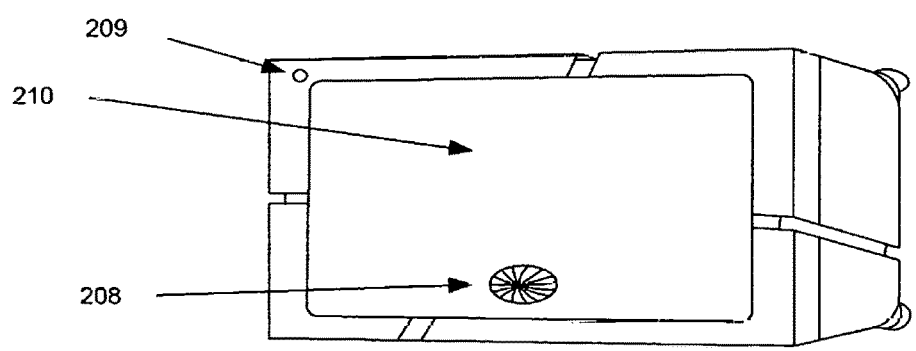
FIG. 2B shows a rear view of the smart name tag device box of the augmented system.
Figure 2C:
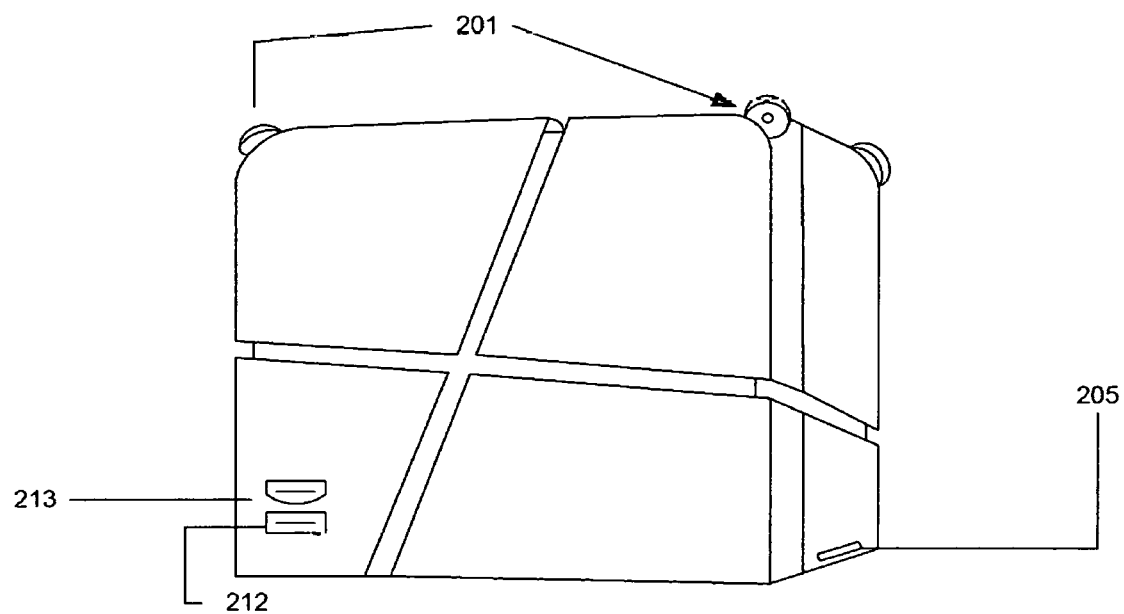
FIG. 2C shows a bottom view of the smart name tag device box of the augmented system.

FIGS. 2A, 2B and 2C illustrates different views of the exemplary embodiments of smart nametag apparatus 200 of the augmented monitoring devices 103, which is a small light weight mobile monitoring and reporting apparatus designed to detect, record and report instances of possible billing fraud, property or prescription drug theft, health risk to a patient and cases of elder or child abuse. The smart nametag apparatus 200 of monitoring devices 103 of system 100 comprises; a wide angle cameras 201 with infrared lights for omnidirectional 360 degree monitoring and recording which placed over the four upper corners of the exemplary embodiment of FIG. 2A at different angles to cover and record as much external environment as possible, a face to face IR camera with lights 202, a microphone 203, a speaker 204, a slot for the SIM card 205, Network connection status LED 206, Battery status LED 207, a fingerprint scanner 208, a secondary IFR camera 209, a color touch screen 210, Micro USB and Power port 211, Micro HDMI port 212 and a GPS unit (not shown) along with this other components which are also included within the exemplary embodiment of the smart nametag apparatus 200 that are not shown in any of the illustrated figures and such components are electronic circuitry of the nametag apparatus consisting of a processor, a memory unit, a rechargeable battery, an internet module, a Wi-Fi module, a RFID receiver and a Bluetooth module.

The smart nametag apparatus 200 of monitoring devices 103 is sized to be worn on user's body as a nametag configured to be mounted in a forward looking location when carried by the caregiver and mounted to the caregiver's body, or on an article of clothing. The smart nametag device 200 of the monitoring devices 103 sends and receives data from the multiple cameras and sensors to and from cloud monitoring and management center 104 of system 100.

According to an embodiment and as mentioned before the smart nametag apparatus is sized to be worn on a caregiver's body as a nametag in which wide angle cameras 201 placed over four upper corners of the embodiment of nametag apparatus 200 is configured for omnidirectional 360 degree monitoring and recording when carried by the caregiver and mounted to the caregiver's body, or an article of clothing.

The microphone 203 within the embodiment of the nametag apparatus 200 is configured to record the audio data such as communication between the caregiver and patient or elderly to detect the abuse, when the nametag apparatus 200 of the system 100 further embodied with the speakers 204 configured to activate an alarm informing the caregiver of any emergency conditions. Further, the nametag apparatus comprises a slot of a SIM card that allows placement of the SIM within the embodiment of the apparatus allowing it to connect to any available cellular network to communicate and send/receive the augmented data over the network collected by the apparatus 200. According to an embodiment, the nametag apparatus 200 further includes a status LED's such as network connection status LED 206 and a battery status LED 207 that inform the caregiver about the connection of the apparatus with other monitoring devices as well as the cloud monitoring center and the status of the level of charge in the battery respectively.

The fingerprint scanning device 208 housed as a part of body of the smart nametag apparatus 200 is configured to capture one or more fingerprints placed on the main display at the capture location. It is further configured to capture one or more orientations of one or more fingers of a caregivers placed on the main display at the capture location. Logic is provided to the controller of the apparatus 200 to capture the fingerprints of the wearer using the fingerprint sensor. The controller of the nametag apparatus 200 wirelessly transmits the data to the cloud system monitoring center 104 to determine an identity of the wearer using the one or more captured fingerprints. If the fingerprint belongs to an authorized caregiver, the cloud system monitoring center 104 returns a positive UUIBD verification and the nametag apparatus 200 prompts the caregiver to proceed to the next sequence of the authenticity verification stage.

The face to face infrared camera and light 202 and infrared thermal imaging and IFR light 209 located within the housing of the nametag apparatus 200 is configured to be used as a part of (1) a multifactor biometric security sequence for iris recognition of caregiver; (2) for thermal imaging of caregiver's face where the IFR camera detects a body temperature of 38° C. or higher and transfers the image to the processor housed within the apparatus 200 which automatically highlight those area of caregiver's face in bright red as the IFR video is streams to the cloud system monitoring center 104. If a body temperature of the caregiver goes out of range, a speaker 204 housed within the apparatus 200 sounds an alarm and alerts the caregiver as well the processor sends data to the operator of the cloud monitoring center to the prospect of the wearers (caregivers) elevated body temperature which in turns alerts caregiver's employer. The IR and IFR cameras 202 and 209 of the apparatus 200 further configured for thermal imaging of patient under the wearer's care, body temperature indicates multiple health problems. The processor with the analyzing algorithm of the nametag apparatus 200 of the monitoring devices 103 continuously analyzes real time data from the cameras and sensors for irregularities in geospatial movements and human thermodynamics of all objects within the IFR camera field of view including patient and caregivers. By detecting geospatial and temperature changes in the objects, including human thermodynamics shifts in body core temperature of a patient or caregiver, the nametag apparatus 200 of the monitoring devices 103 alerts the monitoring center 104 which in turn alerts all authorized caregivers to, inter alia, vascular dysfunction potentially associated with onset of cardiovascular disease (CVD), for monitoring breast health and changes associated with breast disease, area of chronic pain, inflammation, wound healing and disease is evaluated thermo-graphically to assist with a diagnosis and treatment plan, detects thermal indicators as they relate to infection, inflammation or fibrocystic disease, angiogenic or blood vessel significance that would require further evaluation, undetermined pain disorders such as muscular skeletal disorders including wound healing and chronic pain and impaired peripheral circulation including varicosities, peripheral vascular disease or blood viscosity concerns and neuropathies. The collected human thermodynamic data is used to detect and alert care providers of any anomalies that may require intervention by a caregiver for further evaluation and made available to physicians of the patient for long term diagnosis and care.

Furthermore, The IR cameras 202 and 209 are configured to provide second of the three biometric authentication keys needed for binding the wearer to the monitoring devices 103 to activate the system 100. The Infrared Camera 209 housed within the apparatus 200 gets activated after a successful authentication using the user's fingerprint. The wearer is instructed to point the Infrared (IR) camera 209 towards his/her eyes with respect to the IR camera. A time of exposure by the IR camera for the portion of the IR camera field of view filled by the detected eye is determined. The eye is then illuminated by activating an IR light during the time of exposure and deactivating the IR light after the time of exposure needed to capture an image of one retina of either eye or to scan the selected retina. This IFR image or scan of the wearer's retina is then wirelessly relayed to the cloud system monitoring center 104 where algorithms compares the real time IFR images of the retina with sorted images of the retina associated only to the authenticated fingerprint of the wearer taken in step one of the biometric authentication process. If the collected retina record is that of the fingerprint owner, and belongs to an authorized user the authentication is considered successful and will prompt the wearer to proceed to the next sequence of the system's 100 multifactor biometric security, the pairing of a wearable on-body biometric authentication wristband.

The color touch screen 210 of the nametag apparatus 200 of present embodiment is configured to display name and photograph of the current Caregiver after completing all three steps of biometric authentication, USB and Power port 211 configured to allow the nametag apparatus to connect to other devices of the system using USB cable and also to recharge the rechargeable battery of the apparatus 200 and a micro HDMI port is also configured to allow the apparatus 200 to transfer uncompressed video data and compressed or uncompressed digital audio data to the HDMI compatible system devices 103 and to the monitoring center 104.

Furthermore, the embodiment of the nametag apparatus further comprises of a global positioning system (GPS) receiver which is configured to determine wearer/caregiver's location information in relationship with the wearers/caregiver's movement to, from, and within the patient's location. The method provides for autonomous personal movement tracking, and conserves the battery consumption, and provides longer period of portable unit operation by allowing the GPS to manage power consumption. The GPS tracker (not shown) is designed to communicate at specified time interval with the cloud monitoring system 104. The nametag apparatus 200 is programmed to trigger one or more actions in events where the GPS unit presents real time GPS coordinates data within a predefined proximity of a pre-defined geographic area to the cloud system monitoring center 104. This "Pre-defined geo-fenced area", may include but is not limited to the home of patient location; a circumference from the center of predetermined proximity of the aforesaid predetermined area of the patient's home, or where the caregiver is approaching but still not within the four longitude and latitude pairs that define the predetermined "geo-fenced" area or the apex points of the perimeter of an area of interest in the vicinity of the patient geo-fenced area that is the patient location. In another aspect of the embodiment described herein, another version of a defined geographic area is a single longitude/latitude pair and a predetermined radius of a circular perimeter used to define a single geographic area, a specific room in the patient location. In yet another version of a defined geographic area any number of longitude/latitude pairs can be used to determine the corner points of any area, regardless of the number of line segments bounding the shape defined as lines between any numbers of longitude/latitude pairs that form a closed chain of lines. According to present embodiment of caregiver monitoring system 100, the real world geographic area is typically arranged about or within a residential or institutional environment, for an example, the home of a patient or the room of a patient at home or institution utilizing wide area augmentation system technology.

In the preceding GPS embodiment of the invention is fundamental to its operation and intended use, once the remote cloud monitoring system 104 determines the caregiver to be within the proximity of one of the predetermined perimeters, the geo-fenced areas, the monitoring system 100 remotely implements a method of initiating one or more actions on the wearable devices 103. The method is an aspect of an embodiment, includes, monitoring system 100 that remotely tests a first condition to determine the state of the condition, specifically are the reported fence co-ordinates belong to a specific patient geo-fence location and the location assigned to the authenticated caregiver; testing a second condition, monitoring system 100 remotely determines the state of the second condition; if the first condition is true, then determining the time and date reported by the GPS are consistent with the time and date for the caregiver's scheduled attendance at the verified patient GPS location; if both the first and second states of the conditions are true then; initiating one more actions.

In the particular instance of this GPS embodiment, all power circuitry to the embodiment's video and sound recording devices is managed by the GPS and the main controller housed as part of the first embodiment of the invention. Record "on" and record "off" camera states are controlled exclusively by the GPS and by remotely by the cloud system monitoring station 104. Real time wearer/caregiver location data is transmitted by the GPS to the cloud monitoring system 104 where the data is cross referenced to a database of patient geo-fenced locations and the first and second condition tests are applied to the GPS data. If both conditions are TRUE, the cloud monitoring system 104 transmits a "power on" instruction to the GPS unit for activation of camera and sound recording. This "Power on" condition continues for as long as the caregiver remains within the established GPS perimeters of the patient geo-fenced location. This "power on" condition will allow for the live streaming of video, to the cloud monitoring system 104, the video stream augmented with data collected by the GPS and other embodiments of the system 100 and monitoring devices 103 used to identify both the caregiver and specified patient at the geo-fenced location and provides necessary information for unique encryption of the data.

In the alternate, when the GPS unit reports GPS location coordinates where one of the two or both the required conditions are FALSE and the caregiver no longer within the established GPS perimeter of the patients geo-fenced location, the GPS unit (1) independently "power off"; (2) can be remotely powered off by the cloud monitoring system 104; or (3) independently "power off" within a predetermined time when the GPS detects a communication signal loss with the cloud monitoring system 104.

GPS location detection, geo-fencing location methods and systems 100 and the GPS device power management as described of sensors and cameras housed in the first embodiment of the invention is integral to the purpose of the invention. Certain embodiments of the inventions are only to be in a "power up" and "continues activate reporting state" when within proximity of an approved and known geo-fenced location, and the streamed augmented video data must be uniquely identified. This unique GPS data is quality essential to the primary purpose and reporting of billing fraud and patient abuse in real time and protection of the first amendment right of the caregiver and the patient.

According to an embodiment, the nametag apparatus 200 of the monitoring devices 103 comprises an electronic circuitry board (not shown) that further includes a processor and controller that collects augmented data such as audio, video from the surrounding environment and other biometric sensory data of caregiver, analyzes the augmented data using predefined algorithms and transmits the analyzed augmented and tagged data in real time to the cloud monitoring center 104 where the augmented data get stored and further analyzed in search for billing fraud, drug theft or abuse of patient from caregiver. Moreover, the processor of the nametag apparatus 200 further manages power consumption within the apparatus and minimizes power consumption, when the caregiver is not in the geo-fencing perimeter of the patient or the person allotted to the caregiver for care. Furthermore, a memory unit is included within the embodiment of the nametag apparatus 200 configured to store data temporarily for the processor to analyze it before transmitting it in real time to the cloud monitoring center 104, a rechargeable battery is configured within the electronic circuitry of the apparatus 200 allowing it to be re-charged by connecting using power port 211, an internet module is configured to allow the system to communicate, share, receive data over the internet, a Wi-Fi module configured to allow the wireless monitoring devices 103 to connect the Local Wi-Fi network to communicate in case of cellular network connection loss, and a Bluetooth module configured within the embodiment of the nametag apparatus 200 of the monitoring devices 103 to allow internal connection between all the monitoring devices 103 of system 100.

According to another main exemplary embodiment, the foregoing wireless augmented video system 100 includes a wireless wearable wristband (not shown in any drawing) that is one of the wireless augmented monitoring device 103 designed and configured to pair with the nametag apparatus 200 using Bluetooth to complete caregiver's three stage authentication sequence. The wireless wristband as name states is worn on the wrist of the caregiver and features multiple biometric sensors providing continuous stream of biometric data about the caregiver. The collected data is processed and delivered in real time to the processor of the smart nametag device 200 and which then relays the tagged and augmented data to the cloud monitoring and management center 103.

The wireless wristband of the segmented monitoring devices 103 remotely monitors in real time the general physical and emotional state of the caregiver. According to an exemplary embodiment, the biometric sensors embodied in the wireless wristband provides the following data, inter alia; a photoplethysmography sensor which measures blood volume pulse (BVP) from which heart rate, heart rate variability (HRV) and other cardiovascular features are collected; a 3-axis accelerometer captures motion-based activity, to report disturbance in the caregiver's balance such as fall; (3) an EDA sensor (GSR sensor) electro dermal activity sensor used to measure sympathetic nervous system arousal and to derive features related to stress, engagement and excitement; an infrared thermopile that reads peripheral skin temperature to detect, among other things, fever; and a transdermal transmission sensor to measure blood alcohol levels.

The information collected in the aforementioned wireless wearable wristband is collected by the nametag apparatus 200 of the monitoring devices 103 and relayed to the cloud system monitoring center 104 where it is analyzed and recorded to, among other things: (1) alert the caregiver 102 (wearer), caregiver's employer 105 and cloud system monitoring center 103 that the health of the caregiver 102 may be compromised and may represent a threat to the health of patient 101, a common cold or flu could infect elderly or immunosuppressed cancer or transplant patients; (2) alerts the caregiver's employer 105 and cloud system monitoring center 104 if the caregiver is experiencing unusual physical and mental stress, a sign if possible patient's physical or mental abuse; (3) may have fallen or experienced some other bodily trauma possibly putting the caregiver and patient at risk; and (4) detect unacceptable blood alcohol levels that would compromise the quality of care. This embodiment of the wireless wristband exists solely to ensure that the caregiver do not act as conduit for disease that could prove fatal to those under their care.

For present augmented video monitoring system 100, integral to privacy and security during the use of devices 103 is the requirement that each home healthcare agency operator and each employee caregiver register their profile within the system 100 and obtain respectively a UUID and UUBID for pairing to the augmented video data stream, and to be identifiable to government, non-government or private company charged with real time monitoring of the devices, collection and secure storing and viewing of the uniquely encrypted video data stream and for managing access and distribution of the collected data according to the any terms and conditions and prevailing civil and criminal laws.

Figure 3:
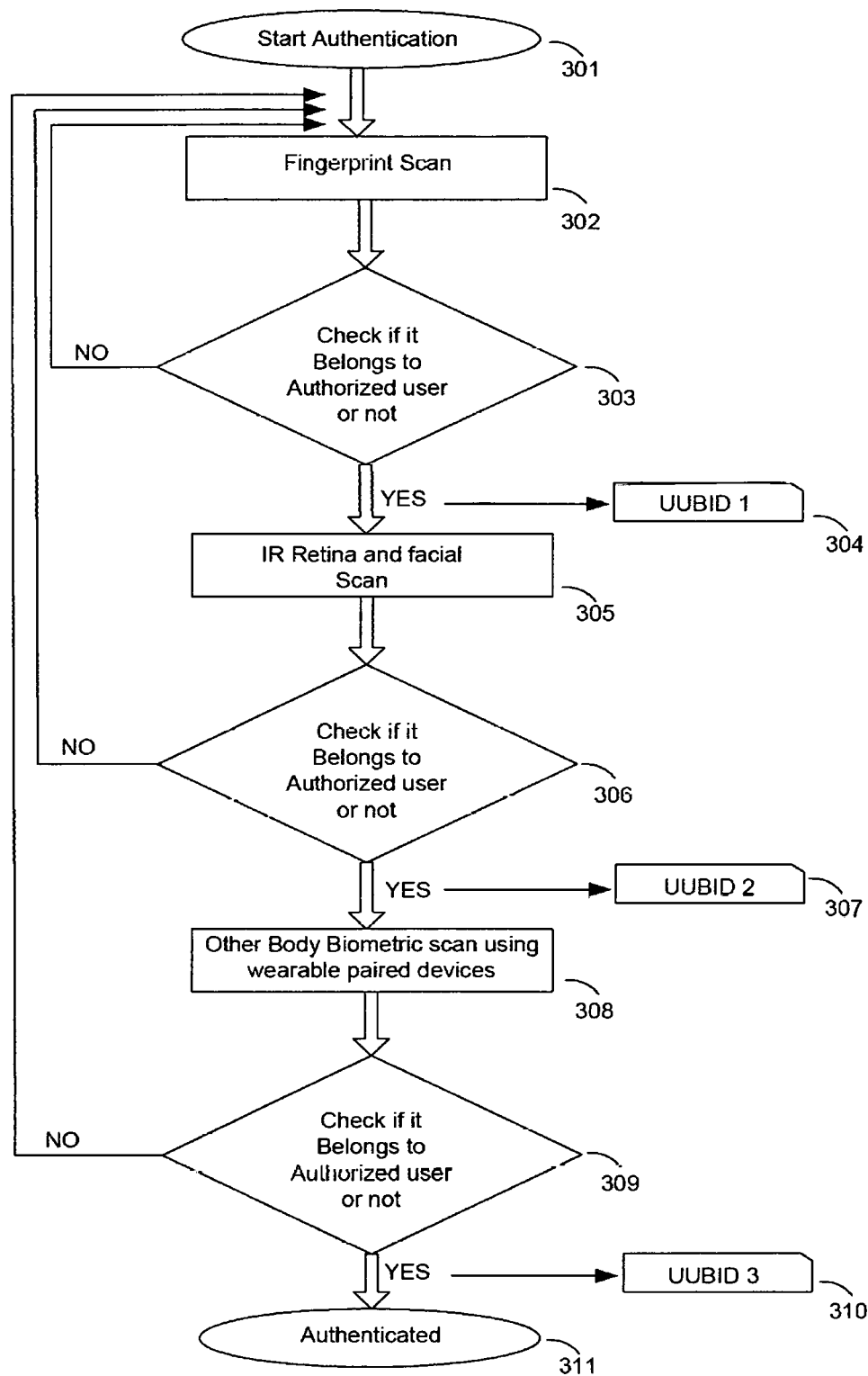
FIG. 3 an exemplarily illustrates the three stage biometric authentication flowchart for the authentication of the user (caregiver) using the wireless augmented system.

FIG. 3 of the present exemplary embodiment, illustrates the three step multifactor biometric authentication flowchart for the authentication of the caregiver using the wireless augmented system, where the already registered caregiver within the system is required to provide three biometric keys to begin the working of the augmented video monitoring system and authentication of the allotted caregiver to specific person in need of care, the biometric keys are encrypted data of fingerprint, facial or Iris and other biometric data received and collected from other wearable devices for example ECG wavelength of caregiver scanned through the wearable wristband that needs to be matched with the registered keys of the caregiver within the system at the time of starting the system by the registered caregiver. According to flowchart of FIG. 3, the caregiver starts the authentication (301) by placing the same finger on the display of fingerprint scanner which was placed at the time of initial registration of the caregiver. The fingerprint scanner 208 of the system 100 scans the fingerprint (302) of the caregiver, collects, encrypts and transmits to the monitoring center 104 where it is checked for its authenticity by comparing it with registered caregiver's data, if it matches with any registered caregiver's data (303), the system monitoring center generates a first UUBID (304) key and transmits signal to the nametag apparatus to start cameras for facial and retina scanning. In the second step of biometric authentication, the thermal IR cameras scans the retina (305) and face of the caregiver and transmits encrypted data to the monitoring center 104 to check if it belongs to the same authorized user or not (306), if it matches then the monitoring center 104 generates a second UUBID key (307) and transmits a signal to pair the nametag apparatus with the wristband and other wearable devices using Bluetooth to measure other body biometrics scan (308) such as for example some specific unique features of Electrocardiogram (ECG) wavelength of the caregiver scanned using the wearable wristband to check if it belongs to authorized user or not (309), if it matches with the key of the same authorized caregiver then the monitoring center generates third biometric authentication key 310 and sends authenticated (322) signal to the monitoring devices 103 of the system 100, and finishes three step authentication process and starts system 100 for real time augmented video monitoring.

The exemplary embodiment requires the monitoring devices 103 to be activated and paired to a caregiver and licensed home healthcare operator using a three step multi-factor biometric verification process, step (1) requires the caregiver to provide the biometric security key previously collected during the registration of the caregiver within the system 100, this requires the caregiver to use the device fingerprint scanner 208 for fingerprint scanning and recognition, the monitoring nametag apparatus 200 collects and transmits this biometric data to the cloud servers of the monitoring body 104 as a UUBID, the first biometric security key, where the system decrypts, isolates and confirms the specific caregiver UUBID against the UUBID stored with the monitoring body 104, the cloud server system then returns a verification code to the nametag apparatus 200 and prompts the apparatus 200 to activate its infrared thermal camera for facial recognition or iris/retina scanning that also collected and transmitted by the devices 103 to the cloud server of the monitoring body 104 as another UUBID, the second biometric security key, which is decrypted, isolated and confirmed by the system 100 for the specific second caregiver UUBID against the UUBID stored in the monitoring body 104 of the same caregiver. After two biometric key authentication, the cloud server system 104 then returns a verification code to the device and prompts the device to activate its Bluetooth connection and pair to a multifactor biometric sensor wristband also worn by the same caregiver user, if no wristband detected, the nametag apparatus 200 will restart the verification again, in third step the nametag apparatus 200 waits for the Bluetooth paired biometric wristband or any other wearable devices to provide certain unique properties of caregiver's electrocardiogram (ECG) for an example as a continues, on-body authentication and then present this new continues biometric data via Bluetooth to the nametag apparatus 200 that now transmits this wristband continues biometric stream as a third security key UUBID to the cloud servers of the monitoring body 104 where the system 100 decrypts, isolates and confirms the caregiver third security UUBID against the data stored with the monitoring body 104, the cloud server system then return a verification code to the device together with profile information on the caregiver to the display on the nametag apparatus 200 color LCD screen 210, this includes the caregiver's name, photo and organization name and employee ID number. The apparatus 200 then remotely instructed by the cloud monitoring system 104 to fully activate and begin continues streaming of selected real time sensor data to the monitoring bodies cloud servers. Any lengthy interruption of the continuous, on-body authentication biometric device will result in the device altering the wearer and the remote monitoring center and eventual self-deactivation of the device and an end to the data transmission, this data is required to validate the claimed healthcare skilled or unskilled service and necessary to obtain payment from an insurance providers or other payer, the absence of this data will result in non-payment.

Figure 4:
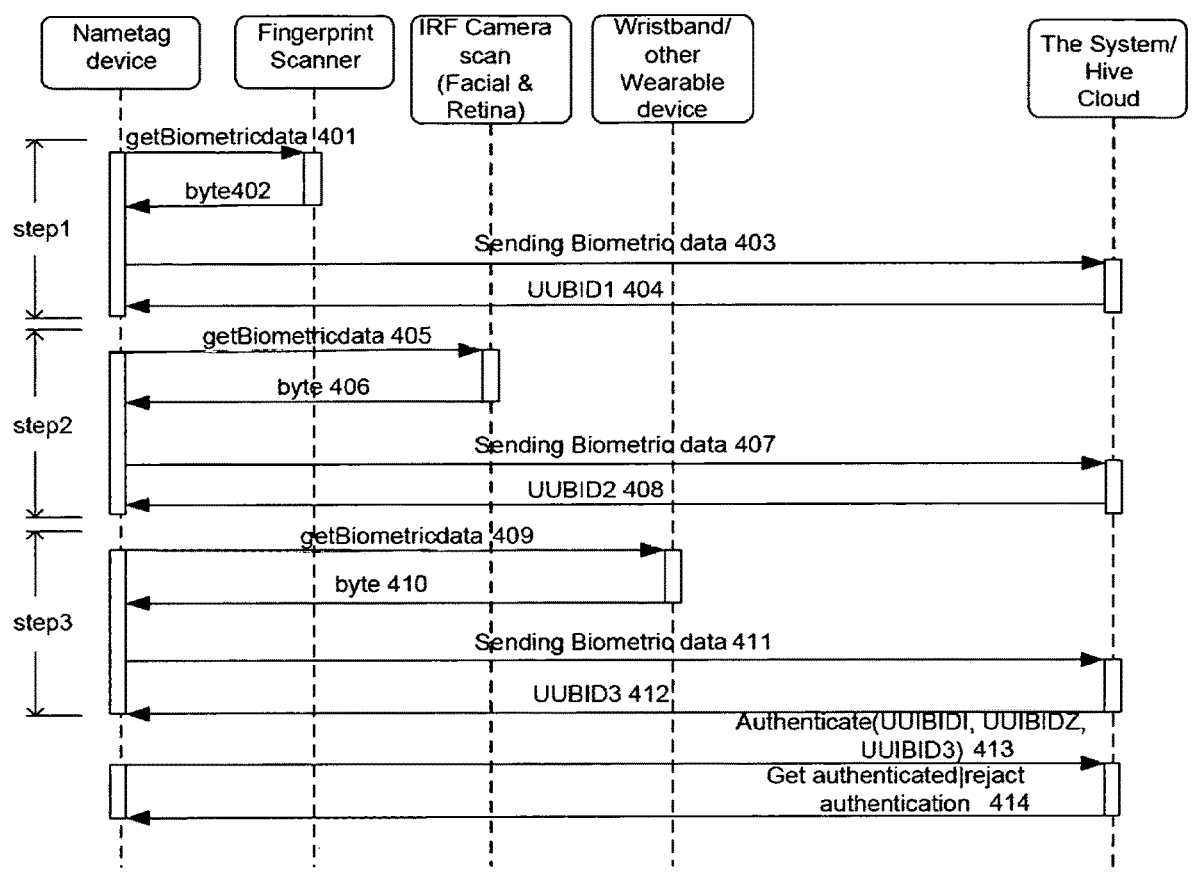
FIG. 4 illustrates simplified diagram of the authentication process of the user (caregiver) of the FIG. 3 using the wireless augmented system.

FIG. 4 of the present embodiment illustrates simplified diagram of the authentication process and method of the user (caregiver) of the FIG. 3 using the wireless augmented system. Where the processor of nametag apparatus 200 in authentication initiation, sends signal of getBiometricData 401 signal to the fingerprint scanner which as a result sends scanned and encrypted data byte 402 of fingerprint to the processor which relays the same to the cloud system monitoring center as a sending biometric data 403 which then decrypts and compares within the database for matching registered profile of the caregiver and if it matches with any registered profile, the monitoring center sends first authentication key UUBID 1 to the nametag device. After the first step of verification the processor starts the IRF camera for retina and facial scanning of the caregiver and sends getBiometricData signal 405 to the IRF cameras which sends the data of scanned retina as a byte 406 as a reply signal, the processor of the nametag device then relays the biometric data of Iris/retina to the cloud monitoring system 104 as a sending biometric data signal 407 and receives a second authentication key from the monitoring center 104 as a UUIBD 2 (408) if the biometric data matches with the data of same caregiver. In the third step of biometric authentication, the processor of the nametag apparatus 200 sends getBiometricData signal 409 to the Bluetooth connected wristbands or other wearable devices and receives encrypted other biometric sensory data in byte as signal 410, which gets relayed to the cloud system monitoring center by the processor of the nametag device 200 as a sending biometric data signal 411 and receives biometric key UUBID3 as a 412 signal from the monitoring center. At the end of the authentication process, the processor sends all three biometric keys UUBID1, UUBID2 and UUBID 3 to the monitoring center for further authentication as a authenticate signal 413 which get analyzed by the center for authenticity and the center sends authenticated signal if all the biometric keys are of same registered caregiver else rejects authentication and sends signal accordingly as signal 414 for further process of monitoring by the system and to avoid billing fraud by the caregivers.

Figure 5:
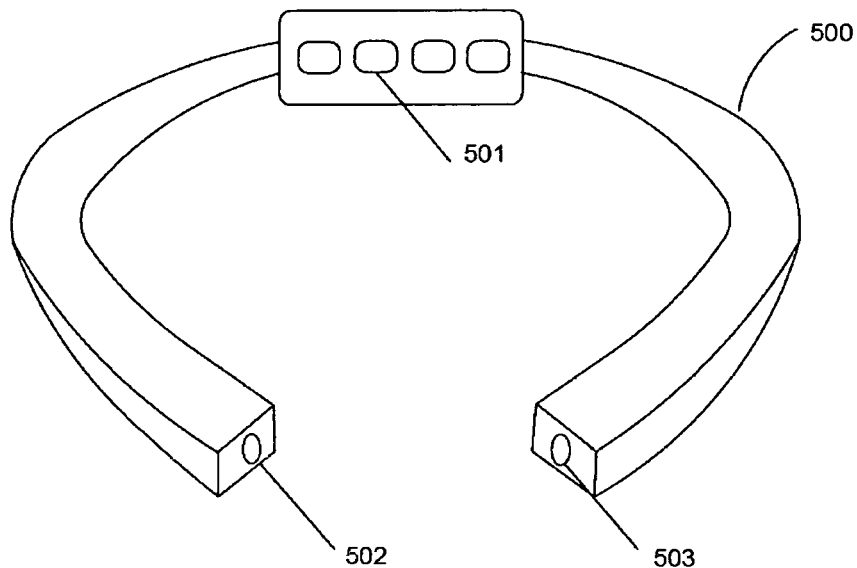
FIG. 5 illustrates another embodiment of wearable monitoring device which is neck wearable device according to embodiment of present invention.

According to one another embodiment of system, the system can be equipped with other devices or embodiments of the devices that are worn by the caregivers or care receiver in the caregiving environment, each of which comprising a plethora of sensors to track a multitude of bio-metric and biomechanical data to establish pattern to ensure caregivers are performing services ordered by the care receiver, further this embodiment of the devices also tracks other data such as GPS location, or departure and arrival time of the caregiver, audio and visual data etc. which is analyzed by the system via artificial intelligence and analytical models that when finds mismatch between the caregiver data, environmental data or billing data, sends a notification to caregiving agencies, billing departments, clients and their respective families. According to present embodiment, the monitoring devices and embodiment of the devices is not limited just to a nametag apparatus or to a wrist wearable device, but without departing from the scope of the invention, the system may use other monitoring devices such as neck wearable device in conjunction with the ear wearable device and other body wearable devices having plethora of sensors and electronic components to provide foregoing application of system of monitoring. Some of such other embodiments of devices of system is described using drawings in details below:

FIG. 5 illustrates another embodiment of wearable monitoring device which is neck wearable device 500 according to embodiment of present invention. The neck wearable 500 with a multitude of sensors ranging from electrode arrays 501, optical 502, visual and audio sensor 503, location (not shown), vibration (not shown) and position sensors (not shown). In this embodiment of the invention, the electrode arrays 501 work in junction with the optical sensors 502, and visual and audio sensors 503 to correlate caregiver action with environmental data taken from the caregiving environment. The electrode arrays 501 serve the purpose of monitoring electrical activity from the spine of the caregiver. It is widely known that when a person performs a certain exercise or movement, electrical impulses from the brain are delivered to organs and limbs via the spinal cord to coordinate the desired motion and balance of the person. In this embodiment of the invention, the electrode array 501 serves the purpose of detecting patterns in electrical impulses when a caregiver performs a certain service such as bathing a patient, or therapeutic services. Data taken by the electrode arrays 501 are correlated to geospatial and thermodynamics environmental and biometric data to record patterns and associate those patterns to specific actions of caregiving such as but not limited to washing hands before treating a patient, physical therapy exercises such as stretching the patient limbs, cleaning tasks such as bathing the patient and in the case of abuse, throwing, punching, or yelling at the patient.

In addition, optical 502, visual and audio sensors 503 work in tandem to monitor the caregiving environment, the actions of the patients and the actions of the caregiver. In one embodiment of the invention, optical imaging can be in the form of thermo-graphic readings where each thermo-graphic image is processed by data processing to assess the patient's well-being. The thermo-graphic images can be used for a wide variety of assessments such as but not limited to detection of diabetic ulcers, infection of wounds, detection of fractures to bone structure, or detection of fevers or probability of illness. Additionally, thermo-graphic imaging may be used to determine if the caregiver sanitized their hands before treating or interacting with the patient physically to deliver therapy or other procedures. In another embodiment of the invention optical imaging can be in the form of UV or black light in the detection of bacteria to reduce the probability of infection. Infrared imaging can be used to monitor and map the geospatial to aid in tracking the movements and actions of objects or persons and used to ensure visibility of the patient even in darkness. In another embodiment of the invention, the visual and optical cameras can also be used to detect differing facial states of the clients or patients via facial recognition data analysis. In this embodiment, a stressed facial expression, a startled facial expression, an upset facial expression, can be detected by facial recognition.

In addition, the electrode array 501 can serve as a method to identify the caregiver and to ensure the caregiver is wearing the device in this embodiment. Identification of a person through the subtle and minute differences in electrical impulse characteristics taken from an electrode array 501 at the spine may be used to identify which caregiver is wearing the device of the invention and if they are wearing it. Like any other physical being, there are minute differences that constituent the personal identity of that being. In this case, the minute differences that are detected are via the electronic impulses sent through the spine wherein amplitude, frequency, and other characteristics of the impulses can be compared to identify each caregiver.

Figure 6:
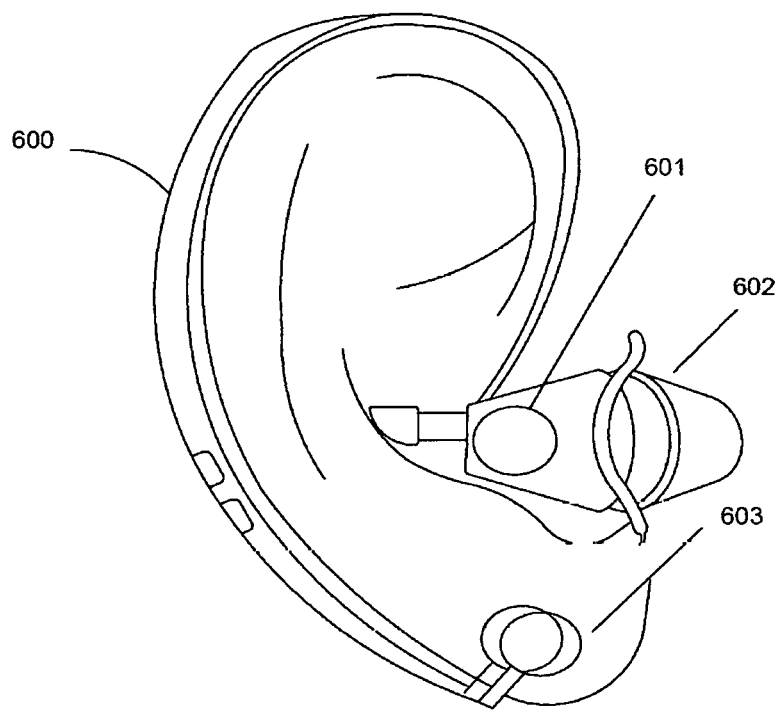
FIG. 6 illustrates an ear wearable embodiment of the wearable augmented monitoring devices according to an embodiment of present invention.

FIG. 6 illustrates an ear wearable embodiment 600 of the wearable augmented monitoring devices according to an embodiment of present invention. The ear mounted device 600 equipped with a visual sensor 601 to take thermographic imaging and near infrared imaging of the client or recipient of services. The visual sensor 601 with the ability to monitor changes in the differing states of the patient, assess well-being, and a plethora of biometric measurements as previously mentioned for the neck worn embodiment.

The optical sensors 601 of the device are used to gather a variety of biometrics of the caregiver like the neck piece 500 to ensure the device is used by the caregiver, and to capture differing actions of the caregiver. In addition, health statistics of the caregiver can be gathered to ensure no illness is spread over to a patient that is elderly or infirmed.

In another embodiment 700 of the invention, the aforesaid monitoring devices 701 can be integrated into the clothing 702 of the caregiver or moved from clothing item to clothing item of the caregiver which is shown in FIG. 7. Clothing 702 can be in the form of but is not limited to a blouse, shirt, pants, jacket, or smock. In this embodiment 700 of the invention, the devices 701 form a network of sensors to track caregiver biomechanical actions, geospatial movements, biometric, dud biomechanical data. In this exemplary embodiment 700, each device can be seen as a node of the entire device 701, where each node may have connectivity to WIFI, a cellular network and communicate with the neck worn or ear worn embodiments of the invention. Each node may also communicate with other nodes to exchange information and to monitor performance of the other nodes. Nodes can be in differing locations, and distance from each other as caregiver bodily characteristics differ from person to person.

FIG. 8A and FIG. 8B illustrates cross sectional view and top view of node 800 and Schematic depicting the form and electronic design of the nodes 800 for a system to detect caregiver actions to prevent elder abuse and healthcare billing fraud where each node 800 may be equipped with wireless charging coils 801, an integrated circuit 802, or sensors 803 on a flexible substrate 804 and an inductor 805. In another design or embodiment of the node 800, they can be incorporated with magnets or an adhesive such as Velcro, to allow placement of the nodes from shirt to shirt or caregiver to caregiver instead of incorporated between the layers of caregiver clothing. Each node can be designed to include a plethora of sensors such as but is not limited to pressure sensors, electrode arrays, micro-electromechanical sensors, motion sensors, optical sensors, audio sensors, and visual sensors. Sensors can be used for a wide variety of purposes such as but not limited to identifying the caregiver, tracking the actions and movements of the caregiver, tracking the GPS location of the caregiver, measuring the biometrics of the caregiver, or measuring biometrics of the client Geospatial movements and biomechanical actions can be correlated to typical caregiver actions, such as but not limited to providing physical therapy, providing hygienic procedures, punching, throwing, or slapping. Each geospatial movement and biomechanical action captured and analyzed by the device incorporated into caregiver clothing can be measured and compared to biometrics of the patient and caregiver to ensure the safety of the caregiver and patient.

According to an exemplary embodiment, the method for mobile application of wireless augmented video system comprises steps which are mere exemplary and not limiting, without departing from the scope of invention steps and sequence can be altered and the steps are: Registration of caregiver or homecare personnel within the system using personal biometric data with other personal details, preferred location for work, previous work track record, experience and specialty. Registration of the caregiver within the system allows the employer of caregivers, monitoring bodies and other organizations such as government organization and insurance companies to monitor the caregiver in real time and detect any billing fraud as well human welfare and care department and law and order department to monitor and analyze caregiver and patient for mental or physical abuse or any property or drug theft; Determination and Geo-fencing of location of person requested for care at home or at any other remote location where the system with the request from the person need in care, detects location and creates Geo-fenced perimeter around the location of that person using the aforesaid methods of four longitude/latitude pair method in which system determines four longitude and latitude pairs around the location of said person and the perimeter covered by that four longitude/latitude pair is counted as Geo-fenced area while in another method, system uses single longitude/latitude pair for location and circle of predetermined radius around the pair is considered as a Geo-fenced area; After Geo-fencing the system allots one or more registered caregiver to the person requested for care by sending information and location of the person to the caregivers; After allotment, the system starts tracking and monitoring real time location of the caregiver with respect to the allotted Geo-fenced location of the person by which system determines and informs the time of work of the caregiver within the Geo-fenced perimeter which allows determination of billing fraud in term of time of service; Verification of biometrics of caregiver with already registered and stored biometric data of same caregiver at Geo-fenced location of patient or person in need of care to initiate functioning of monitoring devices of the system to collect real time environmental data, where the system allows the caregiver to start working within the perimeter of the geo-fenced location after completing three step biometric verification of Fingerprint, Retina/Iris/Facial verification and other from many of aforementioned body biometrics such as, but not limited to, some unique features of ECG waveform of caregiver with the already registered biometrics of same caregiver; Collection of real time Biometric, location and geospatial and thermodynamic environmental data using the monitoring devices of system, where the system allows monitoring and collecting of real time data of Audio data, video data, image data, scanned biometric data of fingerprint, retina, iris, face, real time location data of caregiver with respect of geo-fenced location, and other sensory data such as, but not limited to, Blood Volume Pulse (BVP), 3-axis accelerometer data, electro dermal activity data, skin and body temperature data and blood alcohol level data etc.; Transmitting or relaying the collected real time biometric and geospatial and thermodynamic environmental data to the cloud system monitoring center to receive, store and analyze received data to detect billing fraud, property or drug theft and mental or physical abuse to the patient or person in need of care and to inform and alert the caregiver himself, the employer of caregiver, associated government organization, patient and his/her family members or any person or organization associated with system in case of detection of any of the situations such as, but not limited to, billing fraud, property or drug theft and mental or physical abuse to the patient or person in need of care.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A method of a wireless augmented name badge system comprises steps of:
   (a) registration of a caregiver or home care personnel into the wireless augmented name badge system using a personal biometric data and a mobile application;
   (b) determination and geo-fencing of a location of a person or a patient who requested care at home or at remote location by the wireless augmented name badge system;
   (c) allotment of a geo-fenced location for one or more of the registered caregiver to the person or patient who requested care at home or at remote location by the wireless augmented name badge system;
   (d) tracking the registered caregiver in respect of real time location of the registered caregiver within the allotted geo-fenced location of the patient, as collected by the mobile application to determine time of work and tasks completed of the caregiver;
   (e) geospatial and thermal image mapping of area and objects at the location of the person or patient using cameras of a monitoring device and peripheral devices equipped with cameras to provide necessary data to a machine learning artificial intelligence algorithm to monitor all objects and their movements at the location of the patient;
   (f) verification of identity of the registered caregiver by comparing multiple biometric data of the registered caregiver with a stored personnel biometric data of the registered caregiver to initiate functioning of the monitoring devices at the geo-fenced location;
   (g) the monitoring devices initiate collecting and transmitting of the camera data necessary for the machine learning artificial intelligence algorithm to analyze geospatial movements of both the registered caregiver and the patient within the geospatially mapped area together with a infra-red cameras of the monitoring device collecting thermal imaging data to process and analyze the thermal imaging data necessary for determining aspects of the patient's health and illness as well as any actions of the registered caregiver;
   (h) relaying by the monitoring device, real time biometric, geospatial and thermal image camera data as environmental data to a series of cloud to store and analyze the received real time biometric and camera environmental data and a system of algorithms used to detect health issues and physical needs of the patient from the environmental data; wherein the step of collection of the real time environmental data comprises monitoring and collection of a geospatial data to track movements and position of objects including the patient and care provider, the thermal image camera data and the biometric data to identify the patient and caregiver spatial positions, movements and state of health, audio data, video data, image data, scanned biometric data of fingerprint, retina, iris, face, real time location data of the registered caregiver with respect of geo-fenced location, and other sensory data including a blood volume pulse (BVP), a 3-axis accelerometer data, an electro dermal activity data, a skin and body temperature data and a blood alcohol level data;

(i) analysis of the geospatial movements of the registered caregiver to identify billing fraud, property or drug theft and mental or physical abuse to the patient or person in need of care; and (j) informing and alerting an employer of caregiver, an associated government organization, the patient and a family members or any person or associated organization, by the monitoring device, in case of detection of any of the situations of billing fraud, property or drug theft and mental or physical abuse to the patient or person in need of care.

2. The method of claim 1, wherein the step of registration of caregiver or home care personnel using personal biometric data includes biometric data of fingerprints, Retina or Iris, Facial scan and other unique body biometrics of caregiver.

3. The method of claim 1, wherein the step of determination and geo-fencing of location comprises geo-fencing using a perimeter covered by a four longitude and latitude pairs.

4. The method of claim 1, wherein the step of determination and geo-fencing of location comprises geo-fencing using a single longitude or latitude pair and a predetermined radius of a circular perimeter around the location.

5. The method of claim 1, wherein the step of verification of the biometric data comprises three step verification of fingerprint verification, retina, iris and face verification and other unique body biometric verification such as, but not limited to, some unique properties of an Electrocardiogram (ECG) scan and verification.

* * * * *